US012698265B2

(12) United States Patent
Guimaraes et al.

(10) Patent No.: US 12,698,265 B2
(45) Date of Patent: Aug. 4, 2026

(54) PLANT EXTRACTS ENRICHED WITH IPOLAMIIDE DERIVATIVES AS IMMUNOSUPPRESSANTS FOR TREATING IMMUNOLOGICAL DISORDERS

(71) Applicant: ACHÉ LABORATÓRIOS FARMACÊUTICOS S.A., Sao Paolo (BR)

(72) Inventors: Cristiano Ruch Werneck Guimaraes, Sao Paulo (BR); Carlos Eduardo Vitor, Sao Paulo (BR); Lisandra Ravanelli Pessa, Sao Paulo (BR); Romulo Dragani Reis, Sao Paulo (BR); Alessandra Mascarello, Sao Paulo (BR); Fernando Henrique De Souza Gama, Sao Paulo (BR)

(73) Assignee: ACHE LABORATÓRIOS FARMACÊUTICOS S.A., Sao Paolo (BR)

( * ) Notice: Subject to any disclaimer, the term of this patent is extended or adjusted under 35 U.S.C. 154(b) by 0 days.

(21) Appl. No.: 16/486,683

(22) PCT Filed: Feb. 19, 2018

(86) PCT No.: PCT/BR2018/050037
§ 371 (c)(1),
(2) Date: Aug. 16, 2019

(87) PCT Pub. No.: WO2018/148816
PCT Pub. Date: Aug. 23, 2018

(65) Prior Publication Data

US 2020/0231561 A1 Jul. 23, 2020

(30) Foreign Application Priority Data

Feb. 17, 2017 (BR) .......................... 1020170033180

(51) Int. Cl.
*C07D 311/94* (2006.01)
*A61P 37/06* (2006.01)
*C07C 51/47* (2006.01)
*C07C 59/90* (2006.01)
*C07C 59/92* (2006.01)

(52) U.S. Cl.
CPC ............ *C07D 311/94* (2013.01); *A61P 37/06* (2018.01); *C07C 51/47* (2013.01); *C07C 59/90* (2013.01); *C07C 59/92* (2013.01)

(58) Field of Classification Search
CPC .................................................... C07D 311/94
See application file for complete search history.

(56) References Cited

U.S. PATENT DOCUMENTS

| | | | | |
|---|---|---|---|---|
| 3,703,543 | A | 11/1972 | Alburn et al. | |
| 7,501,222 | B2 * | 3/2009 | Lee .................. | C08F 220/1811 430/270.1 |
| 2010/0028400 | A1 * | 2/2010 | Queiroz Ferreira . | A61K 31/352 424/422 |
| 2018/0071356 | A1 | 3/2018 | Queiroz Ferreira | |
| 2018/0071357 | A1 | 3/2018 | Queiroz Ferreira | |
| 2019/0134136 | A1 | 5/2019 | Queiroz Ferreira | |
| 2020/0231561 | A1 | 7/2020 | Guimaraes et al. | |

FOREIGN PATENT DOCUMENTS

| | | | |
|---|---|---|---|
| CA | 2976583 | | 8/2016 |
| CN | 103120699 | | 5/2013 |
| CN | 103690551 | | 4/2014 |
| DE | 19644422 | | 4/1998 |
| EP | 0045837 | | 2/1982 |
| EP | 1145709 | | 10/2001 |
| EP | 1371372 | | 12/2003 |
| EP | 4001270 | | 5/2022 |
| JP | H03-066682 | A | 3/1991 |
| JP | 2008-024670 | A | 2/2008 |
| JP | 2010-518127 | A | 5/2010 |
| WO | WO 03/094946 | | 11/2003 |
| WO | WO 2008/098325 | | 8/2008 |
| WO | WO 2016/128471 | | 8/2016 |
| WO | WO-2018148816 | | 8/2018 |

OTHER PUBLICATIONS

Dorwald F. A. Side Reactions in Organic Synthesis, 2005, Wiley: VCH, Weinheim p. IX of Preface p. 1-15.*
McElvain, Journal of the American Chemical Society (1941), 63, 1558-63.*
Breslow, Beyond the Molecular Frontier: Challenges for Chemistry and Chemical Engineering, The National Academies Press, 2003 Chapter 5, pp. 55-70.*
Candish, Organic & Biomolecular Chemistry (2011), 9(23), 8182-8189.*
Yalcin, Helvetica Chimica Acta 2007, 90(2), 332-336 Guvenalp, Turkish Journal of Chemistry (2006), 30(3), 391-400.*
Guvenalp, Turkish Journal of Chemistry (2006), 30(3), 391-400.*
Bianco, Gazzetta Chimica Italiana 1976, 106, 947-952.*
Bianco, Tetrahedron, 11, 847-850, 1977.*
Demirci "Anticandidal pimaradiene diterpene from Phlomis essential oils" C. R. Chimie 12 (2009) 612-621.*
James, A. N. "Terpenoids. XLVII. The structure of genipin." Journal of Organic Chemistry, 1961, 26, 1192-206.*
Goldstein, S. "A short, economical, and stereoselective route to prostaglandins by vicinal alkylation of cyclopentadiene." Journal of the American Chemical Society, 1981, 103(15), 4616-18.*
Frank, Scott A "The Vinylogous Intramolecular Morita-Baylis-Hillman Reaction: Synthesis of Functionalized Cyclopentenes and Cyclohexenes with Trialkylphosphines as Nucleophilic Catalysts." Journal of the American Chemical Society, 2002, 124(11), 2404-2405.*

(Continued)

*Primary Examiner* — David K O'Dell
(74) *Attorney, Agent, or Firm* — B. Aaron Schulman, Esq.; Stites & Harbison, PLLC

(57) ABSTRACT

The invention describes extracts from plants of the genus *Stachytarpheta* enriched with ipolamiide derivatives as immunosuppressants for treating immunological disorders. The isolated active compounds and a process of producing these are also disclosed.

15 Claims, 4 Drawing Sheets

(56) References Cited

OTHER PUBLICATIONS

Figure 1:
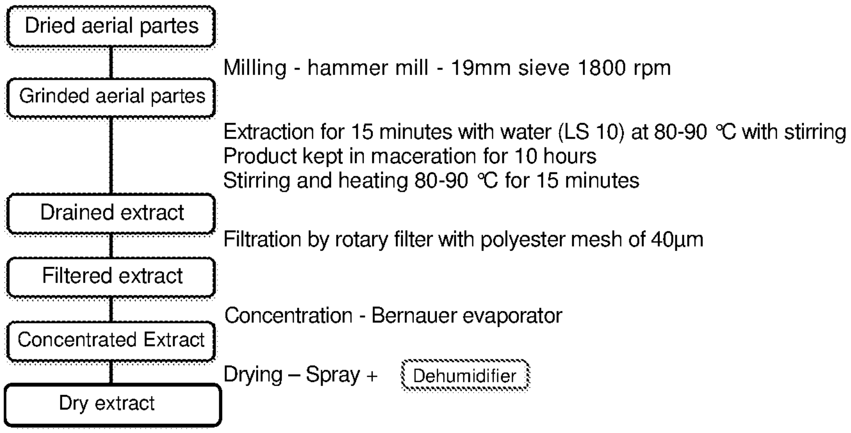

STN Abstract 1964 : 61044 Document No. 60:61044 for Benkeser, Robert A. "Factors governing orientation in metalation reactions. III. Metalation of alkylferrocenes." Journal of the American Chemical Society, 1964, 86(5), 890-5 (STN abstract only).*
Ende "Cyclopentadiene: The Impact of Storage Conditions on Thermal Stability" Organic Process Research & Development 2007, 11, 1141-1146.*
Adebajo et al., "Hypoglycaemic Constituents of Stachytarpheta cayennensis leaf," Planta Medica, Feb. 2007, 73(3): 241-250.
Akkol et al., "Antinociceptive and anti-inflammatory activities of some *Linaria* species from Turkey," Pharmaceutical Biology, Mar. 2009, 47(3): 188-194, 2009, pp. 188-194.
Baden et al., "Differing patterns of sequestration of iridoid glycosides in the Mecininae (Coleoptera, Curculionidae)," Chemoecology, Mar. 2012, 22(2): 113-118.
Benkeser et al., "Factors Governing Orientation in Metalation Reactions. III. The Metalation of Alkylferrocenes," Journal of The American Chemical Society, Mar. 1964, 86(5): 890-895.
Bianco et al., "Acid-catalyzed rearrangements of iridoid aglycones. I—behaviour of lamiidol, a non natural lamiide derivative," Tetrahedron Letters, 1978, 19(48):4829-4832.
Elmasri et al., "Iridoid glycoside permethylation enhances chromatographic separation and chemical ionization," Rapid Communications in Mass Spectrometry, Jul. 2016, 30(18): 2033-2042.
Hoki et al., "Chiral Molecular Motors Ignited by Femtosecond Pump—Dump Laser Pulses," J. Phys. Chem. B, Mar. 2004, 108(15): 4916-4921.
Hoki et al., "Mechanism of unidirectional motions of chiral molecular motors driven by linearly polarized pulses," J. Chem. Phys., Dec. 2003, 119(23):12393-12398.
Khobrakova et al., "Immunomodulating Activity of Extract of Gentiana Algida Pall.," Pharmaceutical Chemistry Journal, Sep. 2017, 51(5):384-387.
Kobayashi et al., "Inhibitory effects of geranium essential oil and its major component, citronellol, on degranulation and cytokine production by mast cells," Bioscience, Biotechnology, and Biochemistry, 2016, 80(6): 8 pages.
Lee et al., "Anti-inflammatory Activities of Chopi (Zanthoxylum piperitum A.P. DC) Essential Oil: Suppression of the Inducible Nitric Oxide Synthase and Cellular Adhesion," Food Science and Biotechnology, 2009, 18(6): 1371-1378.
Lee et al., "Composition and anti-inflammatory activities of Zanthoxylum schinifolium essential oil: suppression of inducible nitric oxide synthase, cyclooxygenase-2, cytokines and cellular adhesion," Journal of the Science of Food and Agriculture, Jun. 2009, 89(10): 1762-1769.
Leitao et al., "Step-Gradient CCC Separation of Phenylpropanoid and Iridoid Glycosides from Roots of Stachytarpheta cayennensis," Journal of Liquid Chromatography & Related Technologies, 2005, 28(12-13): 2053-2060.
Orhan et al., "Immunomodulatory properties of various natural compounds and essential oils through modulation of human cellular immune response," Industrial Crops and Products, Mar. 2016, 81: 117-122.
PCT International Preliminary Report on Patentability in International Appln. No. PCT/BR2018/050037, dated Aug. 1, 2019, 79 pages.
PCT International Search Report and Written Opinion in International Appln. No. PCT/BR2018/050037, dated Sep. 19, 2018, 31 pages.
Schapoval et al., "Antiinflammatory and antinociceptive activities of extracts and isolated compounds from Stachytarpheta cayennensis," Journal of Ethnopharmacology, Feb. 1998, 60(1): 53-59.
Schlogl et al, "Ferrocenasymmetrie, 1. Mitt.: Darstellung und Racematspaltung von asymmetrischen Aminen und Aldehyden der Ferrocenreihe," Monatshefte für Chemie und verwandte Teile anderer Wissenschaften, Mar. 1964, 558-575 (with English translation).
Viccini et al., "Ipolamiide and fulvoipolamiide from Stachytarpheta glabra (Verbenaceae): A structural and spectroscopic characterization," Journal of Molecular Structure, Mar. 2008, 875(1-3): 27-31.
Yu et al., "A new linear monoterpene from the Chinese mangrove plant Cerbera manghas L," Journal of Chinese Pharmaceutical Sciences 18(3), 2009, 232-235.
Aug. 15, 2023, Japanese Notice of Allowance issued for related JP Application No. 2019-544005.
Enders, et al. "Asymmetric Synthesis of (R,S)-Dehydroiridodial, (R,S)-Dehydroiridodiol and Analogues", 1997, pp. 485-493, Liebigs Annl Recueil.
Office Action dated Jan. 2, 2026 in corresponding Canadian Application No. 3,259,255.
Munkert, et al. "Iridoid Synthase Activity Is Common among the Plant Progesterone 5-Reductase Family", Jan. 5, 2015, pp. 136-152, Molecular Plant 8/1.
Damtoft, et al., "Biosynthesis of Iridoid Glucosides in Hebenstretia Dentata", Feb. 10, 1992, pp. 3839-3843, vol. 31, No. 11, Phytochemistry.
Bouyssi, et al, "Intramolecular Carbocupration Reaction of Unactivated Alkynes Bearing a Stabilized Nucleophile: Application to the Synthesis of Iridoid Monoterpenes", Feb. 12, 1999, pp. 1297-1300, Tetrahedron Letters 40/7.
Zimmermann, et al, "Stereoselective synthesis of trans-fused iridoid lactones and their identification in the parasitoid wasp Alloxysta victrix, Part I: Dihydronepetalactones",Aug. 7, 2012, pp. 1246-1255, vol. 8, Beilstein Journal of Organic Chemistry.
Miettinen, et al, "The seco-iridoid pathway from Catharanthus roseus" Apr. 7, 2014, pp. 1-12, Nature Communications 5/1.
Office Action dated Feb. 24, 2026 in corresponding Canadian Application No. 3,,052,713.

* cited by examiner

PLANT EXTRACTS ENRICHED WITH IPOLAMIIDE DERIVATIVES AS IMMUNOSUPPRESSANTS FOR TREATING IMMUNOLOGICAL DISORDERS

FIELD OF THE INVENTION

The following invention describes novel and inventive isolated compounds and extracts with immunosuppressive activity and a process of producing compounds from ipolamiide and extracts, from plants of the genus *Stachytarpheta*. In this way, the present application also describes novel and inventive compositions and their use for the treatment of immunological disorders. The present invention is in the fields of pharmacy, medicine and chemistry.

BACKGROUND OF THE INVENTION

Immunological Disorders

Immunological disorders can be considered as any imbalance or malfunction of the immune system. This system is primarily responsible for assisting in the defense of the body against external or unknown agents through antibodies that recognize and fight harmful antigens.

Autoimmune diseases are an example of immunological disorders in which the organism starts to produce antibodies against their own molecules, making no distinction between endogenous and exogenous agents. In such cases, medicaments with immunosuppressive activity would be highly demanded to help patients relieve the symptoms caused by this type of disorder.

Autoimmune diseases, except for rheumatoid arthritis and autoimmune thyroiditis, are individually rare, but together they affect approximately 5% of the population of the western countries. Their etiology is not fully understood. In organ-specific and systemic autoimmune diseases, it is observed a loss of the capacity of the immune system to distinguish what is self from what is not self. This ability, called self-tolerance, is maintained in the immunocompetent B and T cells by both central and peripheral mechanisms. The loss of self-tolerance may have intrinsic or extrinsic causes. Environmental factors such as bacterial and viral infections, exposure to physical and chemical agents such as UV, pesticides and drugs are examples of extrinsic causes. Intrinsic causes, that is, related to characteristics of the individual itself, are usually associated with polymorphisms of histocompatibility molecules, components of innate immunity, such as the complement system and Toll-like receptors, components of acquired immunity as regulatory lymphocytes and cytokines, in addition to hormonal factors which are under genetic control.

The therapeutic strategy in autoimmune diseases mainly consists in suppressing the immunological system using immunosuppressants, which act on the inhibition of the early stages of development of immunity. This therapy does not perform a selective immunosuppression, which led to the development of a variety of antibodies. Biological agents may be employed to inhibit the effect of cytokines, as occurs with anti-cytokine monoclonal antibodies or the use of soluble receptors that bind to the cytokine and block their effects on target cells. The cytokines are also used in biological therapy through analogous recombinant proteins that mimic the effect of the original cytokine. The main therapeutic targets in anti-cytokines therapy are the pro-inflammatory cytokines interleukin-1 (IL-1), TNFα and IL-6, and the main cytokine agonist therapy is performed with the use of type I interferons (IFN). In the type I interferon family, recombinant proteins of IFNα and of IFNβ are used in clinical practice, primarily for the treatment of viral hepatitis (hepatitis virus B and C) and of multiple sclerosis, respectively. For the latter, the proposed mechanism of action is the antagonism that the INFβ exerts against IFNγ, which has great importance in the physiopathology of multiple sclerosis. The IFNα has also been used in the treatment of muco-cutaneous, ocular and neurological manifestations of Behçet's disease and Churg-Strauss syndrome. Fontolizumab is a humanized anti-IFNγ agent, which has been evaluated in patients with abnormalities in dendritic cells with good results.

Monoclonal antibodies have advantages in the treatment of autoimmune diseases when compared with conventional therapies as they are a targeted therapy, with specificity and high selectivity. However, they are used as a second line of treatment when there is no effectiveness in the control of autoimmune diseases with conventional therapies. In addition to restrictions on the efficacy, monoclonal antibodies still have several limitations related to cost and accessibility. Several autoimmune diseases still lack effective treatments, with good tolerability by patients.

Natural products have been used for centuries in the treatment of different diseases. Recently, major efforts have been made in the development of new research of herbal products with immunosuppressive effects. For example, several clinical trials performed in the United States have already shown significant benefits of *T. wilfordii* extract in patients with rheumatoid arthritis. Although there are several species and their active constituents with mechanisms of action described, there is still a vast field to be explored regarding in vitro and in vivo investigations and future clinical trials in immunologically based diseases. These natural products should be formulated in appropriate pharmaceutical compositions in order to ensure the effectiveness of the treatment of autoimmune diseases.

An autoimmune disease for which, so far, there is no effective medication, much less a medication option obtained from natural extracts, can be exemplified by vitiligo. Vitiligo is commonly associated with loss of functional melanocytes and is considered the most common acquired depigmentation disorder in humans, affecting at least 0.5% of the world population. It is characterized by the development of white maculae, resulting from the loss of epidermal melanocytes, which can result in cellular destruction through a specific cytotoxic immune response to melanocytes and in damage to the adhesion system thereof.

Multiple mechanisms have been associated with vitiligo such as genetic predisposition, environmental activations, metabolic anomalies and changes in the immune and inflammatory responses. In addition, conditions such as exposure to ultraviolet radiation and oxidative stress are known to aggravate this condition.

Due to the lack of specific knowledge about the initial onset of the disease, several studies try to elucidate the biological pathways involved in this pathogenesis. Most of them indicate the complexity and the challenges related to such disease, being very difficult to find an efficient treatment. We must not forget that most immunological disorders have an important social impact, causing a high level of psychological stress for the patients. To date, there is no intervention capable of delivering the cure of vitiligo.

In this way, it becomes eminent the need to identify new compounds capable of promoting immunosuppressive activity with long-term effect. Thus, the present invention addresses this gap in the treatment of immunological disorders through novel compounds which, when isolated, demonstrate immunosuppressive activity and active extracts comprising groups of active compounds, which are obtained in an unique and inventive manner.

Highlighting the complexity and lack of scientific knowledge about vitiligo, it was believed so far that the structure of ipolamiide in its intact form could be associated with immunosuppressive activity, relevant to the treatment of patients with vitiligo. However, in the present invention we demonstrate that this activity results from specific derivatives of ipolamiide and of the extracts comprising such compounds, preferably obtained by the unique and inventive processes of production described herein. Both compounds and extracts present immunosuppressive activity confirmed experimentally. This activity is demonstrated herein by blocking the activation of CD8+ T cells and reduction of IFN-□ secretion. This mechanism has been shown to be promising for vitiligo in view of recent clinical findings related to the quantification of these components in the skin of patients. Specifically, high concentrations of CD8+ T cells and IFN-□ are linked to the apoptosis of melanocytes and, therefore, the modulation of these is a promising mechanism of action.

From what can be deduced from the researched literature, no documents were found anticipating or suggesting the teachings of the present invention, so that the technical solution proposed herein has novelty and inventive activity in view of the state of the art.

SUMMARY OF THE INVENTION

The present invention describes novel and inventive compounds derived from ipolamiide, which have immunosuppressive activity. Therefore, they can be used for the treatment of immunological disorders. Additionally, the present invention describes vegetal extracts enriched with said compounds, derived from ipolamiide, obtained through an unique process of production, also having immunosuppressive activity.

It is, therefore, an object of the present invention ipolamiide derivatives comprising compounds of the general formula:

(I)

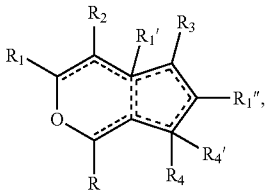

(II)

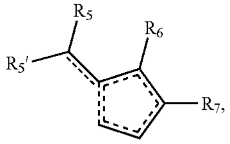

(III)

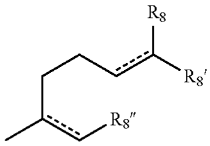

wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$; $R_5$, $R_{5'}$ correspond to H, $CH_3$, $COOCH_3$, CHO, $CH_2OH$; $R_6$ corresponds to CHO, COOH, $COOCH_3$; $R_7$ corresponds to H, $CH_3$; $R_8$, $R_{8'}$, $R_{8''}$ correspond to CHO, $CH_3$, $CH_2OH$, COOH and the dashed bonds represent single (C—C) or double (C═C) bonds between carbons (up to two double bonds per structure).

In a preferred embodiment, at least one preferred compound of the present invention may be selected from the group comprising the following structures:

(IV)

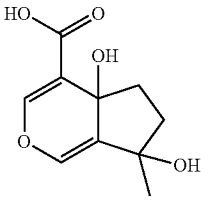

(V)

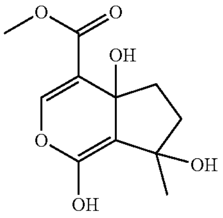

(VI)

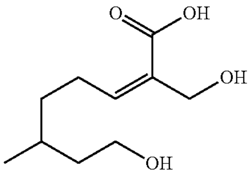

(VII)

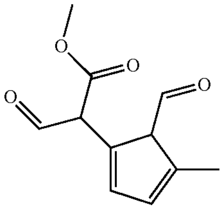

(VIII)

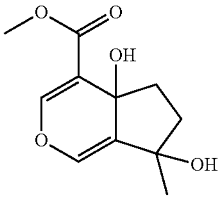

(IX)

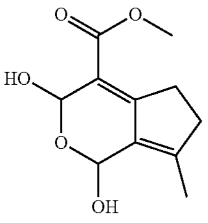

-continued (X)

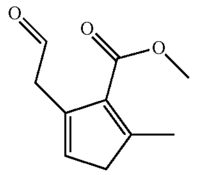

(XI)

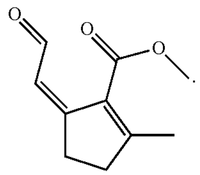

In this preferred embodiment, the compound of general formula (I) comprises the compounds of formula (IV), (V), (VIII) and (IX), the compound of general formula (II) comprises the compound of formula (VII), (X) and (XI) and the compound of general formula (III) comprises the compound of formula (VI).

It is also an object of the present invention a method of treatment of immunological disorders, comprising administering to a patient a compound of general formula (I), (II) and/or (III), in sufficient amount to provide immunosuppressive effect. In a preferred embodiment, the method of treatment is intended for the treatment of vitiligo.

We can, thus, also consider the use of at least one compound of general formula (I), (II) and/or (III) in a composition for treatment of immunological disorders.

Furthermore, it is an object of the present invention a pharmaceutical composition for the treatment of immunological disorders, comprising at least one compound selected among the groups comprising the compounds of general formula:

(I)

a) 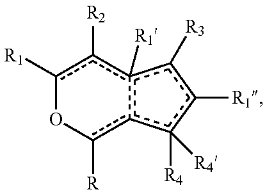

(II)

b) 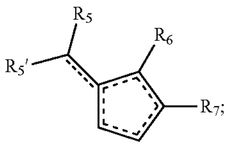 and/or (III)

c) 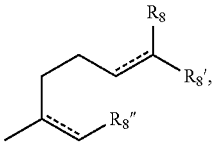

wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$; $R_5$, $R_{5'}$ correspond to H, $CH_3$, $COOCH_3$, CHO, $CH_2OH$; $R_6$ corresponds to CHO, COOH, $COOCH_3$;

$R_7$ corresponds to H, $CH_3$; $R_8$, $R_{8'}$, $R_{8''}$ correspond to CHO, $CH_3$, $CH_2OH$, COOH and the dashed bonds represent single (C—C) or double (C═C) bonds between carbons (up to two double bonds per structure); and d) pharmaceutically acceptable vehicle.

In an optional embodiment, the composition of the present invention further comprises the ipolamiide compound.

In an optional embodiment, the composition of the present invention may further comprise at least one of the following compounds:

(IV)

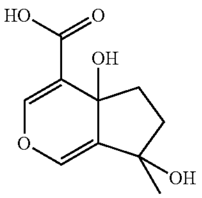

(V)

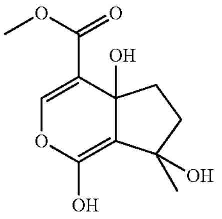

(VI)

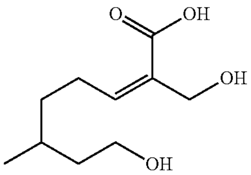

(VII)

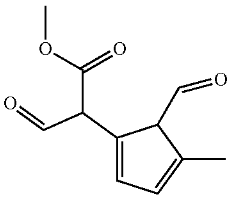

(VIII)

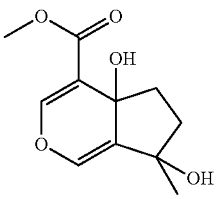

(IX)

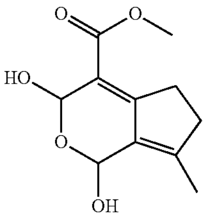

-continued (X)

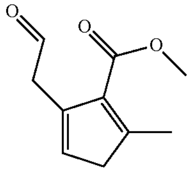

(XI)

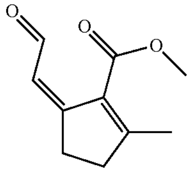

(XII)

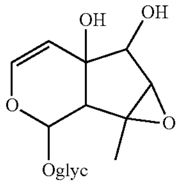

(XIII)

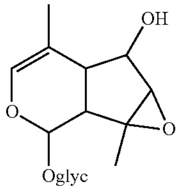

(XIV)

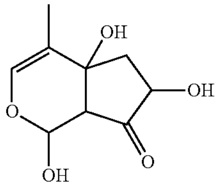

(XV)

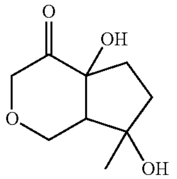

(XVI)

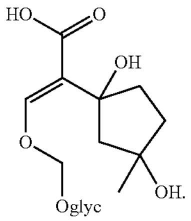

Additionally, the present invention describes the process for production of the compounds of general formula (I), (II) and/or (III), comprising the step of subjecting at least one ipolamiide compound to at least one heating step at high temperatures, in the presence of at least one suitable solvent for a sufficient time to obtain the compounds of the general formulas (I), (II) and/or (III).

In a preferred embodiment, the high temperatures of the present invention comprise temperatures above 35° C., more preferably between 35° C. and 165° C.

In a preferred embodiment, the process of production of the compounds of general formula (I), (II), and/or (III) comprises subjecting at least one ipolamiide compound to at least one hydrolysis and/or solvolysis step. Even more ideally, at least one ipolamiide compound is subjected to an acid hydrolysis step. Optionally, at least one ipolamiide compound is subjected to an alkaline/basic hydrolysis step.

As previously mentioned, we verified that isolated ipolamiide does not demonstrate immunosuppressive activity. On the other hand, certain groups of compounds derived from ipolamiide have such activity. At the same time, we have also specified the advantages of obtaining herbal medicines for the treatment of diseases, since these compound production systems allow a series of productive interactions between the components of the plant and the active compounds, often even synergistically. Thus, to additionally obtain an herbal medicine comprising such active compounds, we have developed an unique production process which allows to obtain an extract enriched with compounds of interest. As described below, the extract production process of the present invention comprises unique steps that lead to extracts enriched with the ipolamiide derivatives with immunosuppressive activity. We verified the relevance of preselecting input vegetal biomasses containing between 2.5% and 3.5% of ipolamiide, resulting in an extract enriched with ipolamiide and compounds derived from ipolamiide from about 1% to about 20%, preferably from about 8.5% to about 11.5% of content of ipolamiide and derivatives.

As previously presented, the vegetal biomass containing this compound will be used as starting material for the production process of the extract. Only with the production process of the present invention it is possible to obtain an extract enriched with specific compounds derived from ipolamiide. This enriched extract, further, presents immunosuppressive activity.

It is, therefore, an additional object of the present invention a process for production of extract enriched with compounds derived from ipolamiide, comprising essentially the steps of:

a) selecting input vegetal biomass with a content of ipolamiide between 2.5% and 3.5% obtained from plants of the genus *Stachytarpheta;*
b) submitting the selected biomass from a) to oven drying at temperature between 40 to 80° C., until obtaining the humidity stabilization between 10 to 12%;
c) milling the vegetal biomass;
d) performing the extraction of the vegetal biomass through the steps of:
i. heating of the vegetal biomass at a temperature between 70 to 100° C., with constant stirring;
ii. maceration of the vegetal biomass at room temperature;
iii. heating of the vegetal biomass with temperature between 70 to 100° C.

In a preferred embodiment, the process for production of the present invention further comprises the steps of:

iv. filtering and concentration of the extract;
v. drying in Spray Dryer, during 1 to 60 seconds, with inlet temperature between 155 and 165° C. and outlet temperature between 85 to 95° C., coupled to a dehumidifier.

In a preferred embodiment, the process for extraction of the present invention is an aqueous or hydroalcoholic process, even more preferably aqueous process.

Therefore, the process for production of the present invention allows to obtain a standardized extract enriched with compounds derived from ipolamiide, preferably with a yield of about 8% to about 10%.

It is, therefore, an additional object of the present invention the extract enriched with compounds derived from ipolamiide obtained by the above-mentioned procedure. The standardized extract enriched with compounds derived from ipolamiide of the present invention comprises, preferably, the compounds of formula (I), (II) and/or (III).

The vegetal biomass of the present invention comprises all parts of plants of the genus *Stachytarpheta*. Preferably, the vegetal biomass comprises the aerial parts of the plants, more preferably, the leaves.

In a preferred embodiment, the input vegetal biomass comprises at least one vegetal biomass with uniform content of ipolamiide between 2.5% and 3.5%. In an optional embodiment, the input vegetal biomass comprises more than one vegetal biomass, wherein the different vegetal biomasses have different contents of ipolamiide independently, but together achieve an uniform content of ipolamiide (between 2.5% and 3.5%).

In another preferred embodiment, the actual content of ipolamiide in the input vegetal biomass can be used as a parameter for predicting the theoretical content of ipolamiide and derivatives in the extract obtained. This prediction can be accomplished by a method comprising the step of applying Equation I to some parameters obtained experimentally to find the ideal proportions of ipolamiide in the input vegetal biomass, which preferably projects the content of ipolamiide and derivatives in the extract from 8.5% to 11.5% of. The Equation I is defined below:

% Theoretical content of ipolamiide and derivatives in the extract=% Actual content of ipolamiide in the vegetal biomass×DER/(<actual content of ipolamiide and derivatives in the extract/actual content of ipolamiide in the input vegetal biomass>)±standard deviation (Equation I).

In this way, it is possible to predict the theoretical content of ipolamiide and derivatives in the extract from the actual content of ipolamiide in the input vegetal biomass. Preferably, the ratio between the actual content of ipolamiide and derivatives in the extract/content of ipolamiide in the input vegetal biomass is between about 3.0 and about 3.5.

In an embodiment even more preferred, the plants of the present invention comprise *Stachytarpheta cayennensis*.

It is, therefore, an additional object of the present invention the use of standardized extract enriched with compounds derived from ipolamiide, obtained from plants of the genus *Stachytarpheta* for the manufacture of a medicament with immunosuppressive activity.

It is, therefore, an additional object of the present invention at least one active fraction of extract enriched with compounds derived from ipolamiide. Preferably, at least one fraction comprises at least one compound derived from ipolamiide of formula (I), (II) and/or (III).

In an optional embodiment, the active fraction of enriched extract further comprises ipolamiide.

It is, therefore, an additional object of the present invention the use of at least one standardized fraction enriched with compounds derived from ipolamiide, obtained from plants of the genus *Stachytarpheta* for the manufacture of a medicament with immunosuppressive activity.

These and other objects of the invention will be readily appreciated by those skilled in the art and by the companies having interests in the segment, and will be described in sufficient detail for its reproduction in the following description.

DETAILED DESCRIPTION OF THE FIGURES

FIG. 1—Summary flowchart describing the production process of the active extract enriched with ipolamiide derivatives obtained from *Stachytarpheta cayennensis*.

Figure 2:
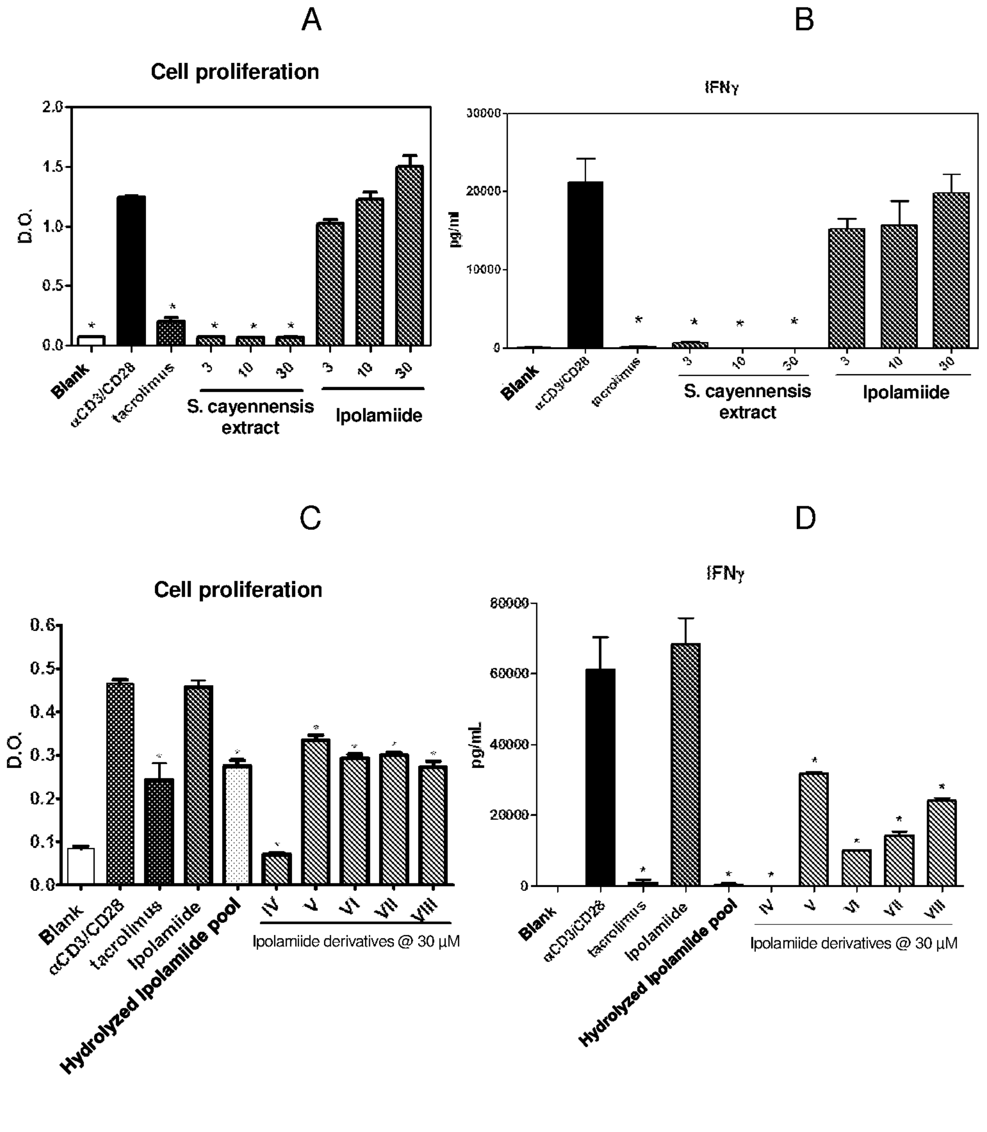

FIG. 2—Effect of the aqueous extract of *Stachytarpheta cayennensis* (3, 10 and 30 μM, concentration expressed in ipolamiide) and isolated ipolamiide (3, 10 and 30 μM) on the proliferation of CD8+ T cells activated by αCD3/CD28 (A) and IFNγ production (B). The effect of the pool of compounds (IV to VIII) and the five novel isolated compounds (IV to VIII) generated after the acid hydrolysis of ipolamiide (30 μM) was also evaluated in the same experiments, proliferation of CD8+ T cells activated by αCD3/CD28 (C) and IFNγ production (D). Tacrolimus (0.5 μM) was used as the positive control for all experiments. The data are the mean±SD of three replicates.

Figure 3:
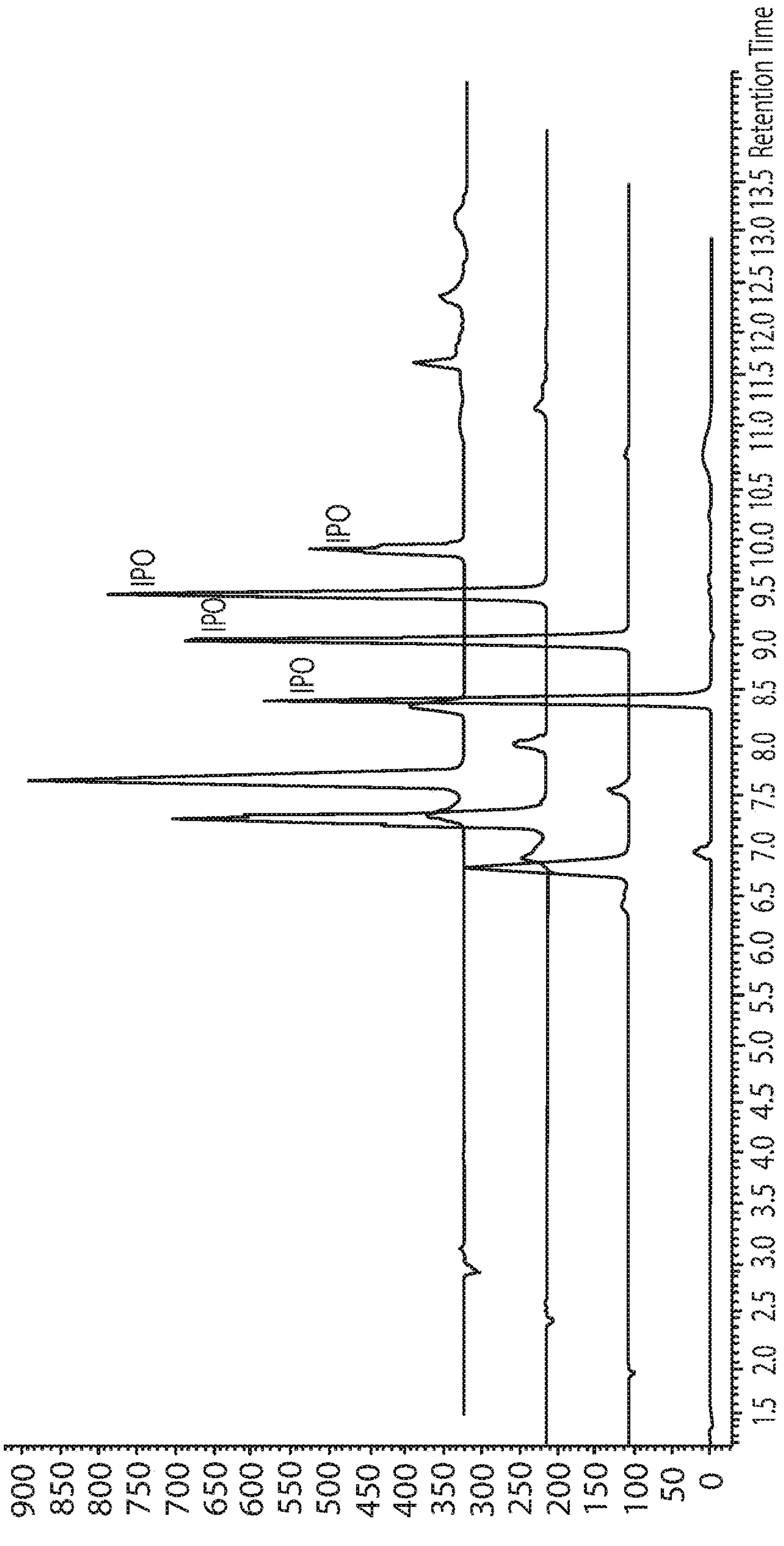

FIG. 3—Effect of the acid hydrolysis of ipolamiide on the formation of its derivatives. Chromatogram of intact ipolamiide (blue); Ipolamiide hydrolyzed at 0.1 N HCl at 40° C. for 1 h (green); Ipolamiide hydrolyzed at 0.1 N HCl at 40° C. for 2 h (red); Ipolamiide hydrolyzed at 0.1 N HCl at 40° C. for 5 h (magenta). IPO=Ipolamide.

Figure 4:
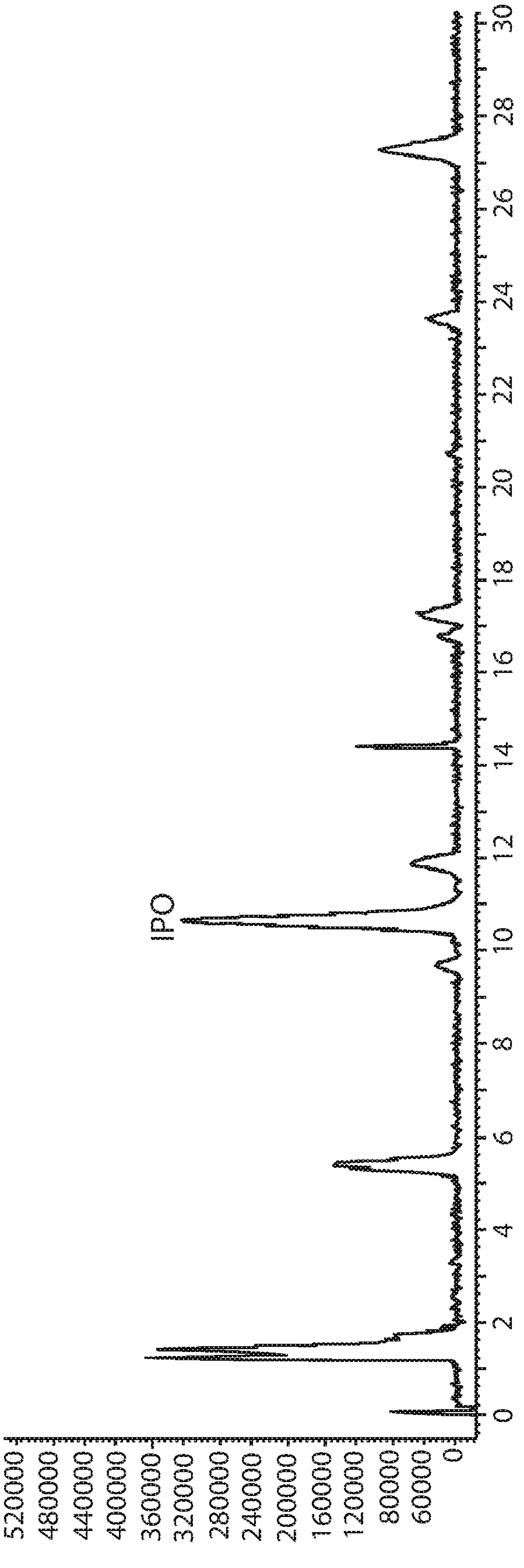

FIG. 4—Chromatogram of the *Stachytarpheta cayennensis* extract obtained from the production process claimed herein. The figure illustrates the ipolamiide marker and its specific derivatives at retention times: 5.5; 9.7; 12.0; 14.3; 17.3 min. IPO=Ipolamiide.

DETAILED DESCRIPTION OF THE INVENTION

The examples shown herein are for the sole purpose of exemplifying one of several ways of carrying out the invention, however, without limiting the scope thereof.

Active Compounds

The present invention presents novel and inventive compound groups, comprising the following general formulas:

(I)

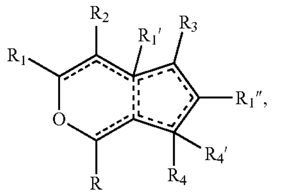

(II)

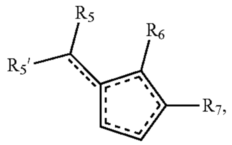

(III)

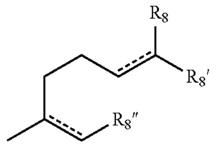

wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$; $R_5$, $R_{5'}$ correspond to H, $CH_3$, $COOCH_3$, CHO, $CH_2OH$; $R_6$ corresponds to CHO, COOH, $COOCH_3$; $R_7$ corresponds to H, $CH_3$; $R_8$, $R_{8'}$, $R_{8''}$ correspond to CHO, $CH_3$, $CH_2OH$, COOH and the dashed bonds represent single (C—C) or double (C═C) bonds between carbons (up to two double bonds per structure).

Example 1

The compounds of general formula (I) comprise the following structures.

A

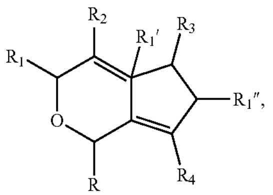

B

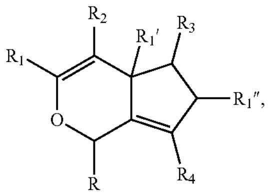

C

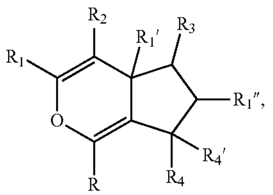

Example 2

The compounds of general formula (II) comprise the following structures.

D

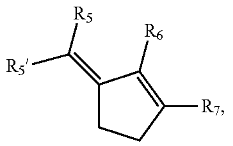

E

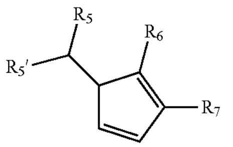

F

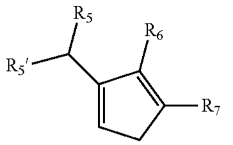

-continued

G

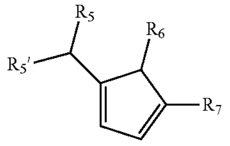

Example 3

The compounds of general formula (III) comprise the following structures.

H

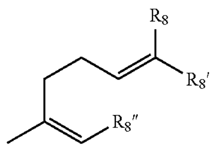

I

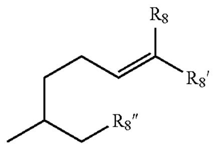

J

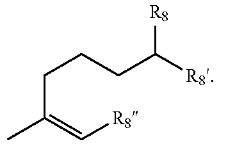

Those above mentioned structures exemplify chemical structures backbones included in formulas (I), (II) or (III).

Immunological Disorders

The term "immune disorders" of the present invention comprises any dysfunction of the immune system. Commonly the disorders can be characterized by the components of the immune system that are affected or by the level of activity of the immune system. In the present invention, preferably, the immune disorders refer to diseases that have some evidence of autoimmunity. We can consider in the present invention vitiligo as being even more preferably chosen among the possible immune disorders.

Method of Treatment of Immune Disorders

The present invention describes a method of treatment of immune disorders, comprising administering to a patient a compound of general formula (I), (II) and/or (III), in sufficient amount to provide immunosuppressive effect. It should be noted that, for the purpose of the present patent application, the treatment of immune disorders can be achieved using ipolamiide derivatives and/or fractions and/or extracts containing ipolamiide derivatives, any of these having immunosuppressive activity. In a preferred embodiment, the method of treatment is intended for the treatment of vitiligo.

Pharmaceutical Composition Comprising Isolated Compounds Derived from Ipolamiide.

In one embodiment, the pharmaceutical composition of the present invention comprises isolated ipolamiide derivatives, used alone or in combination, for the treatment of immune disorders, wherein the compounds comprise at least one compound selected from the group comprising:

a)

(I)

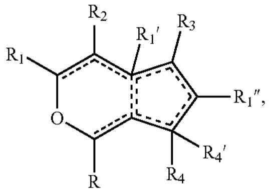

b)

(II)

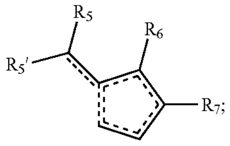

and/or c)

(III)

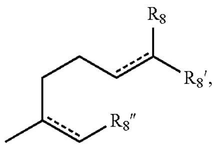

wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$; $R_5$, $R_{5'}$ correspond to H, $CH_3$, $COOCH_3$, CHO, $CH_2OH$; $R_6$ corresponds to CHO, COOH, $COOCH_3$; $R_7$ corresponds to H, $CH_3$; $R_8$, $R_{8'}$, $R_{8''}$ correspond to CHO, $CH_3$, $CH_2OH$, COOH and the dashed bonds represent single (C—C) or double (C═C) bonds between carbons (up to two double bonds per structure); and d) pharmaceutically acceptable vehicle.

In an optional embodiment, the above pharmaceutical composition further comprises the ipolamiide compound.

In a preferred embodiment, the pharmaceutical composition of the present invention comprises the compounds:

(IV)

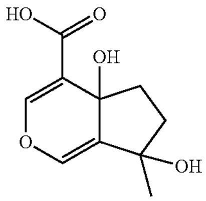

(V)

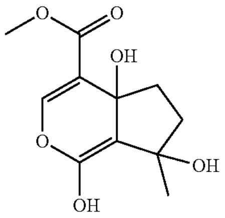

-continued (VI)

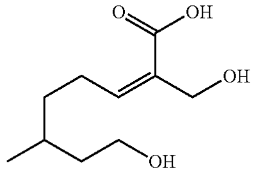

(VII)

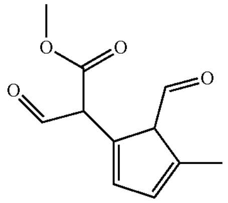

(VIII)

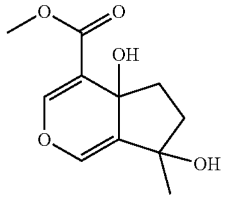

(IX)

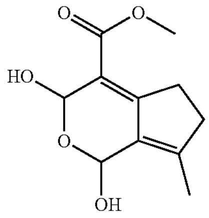

(X)

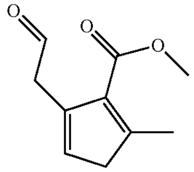

(XI)

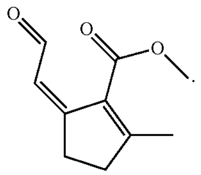

In this preferred embodiment, the compound of general formula (I) comprises the compounds of formula (IV), (V), (VIII) and (IX), the compound of general formula (II) comprises the compound of formula (VII), (X) and (XI) and the compound of general formula (III) comprises the compound of formula (VI).

The pharmaceutical composition of the present invention may additionally comprise the following compounds:

(XII)

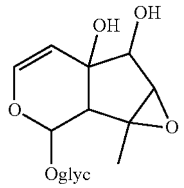

(XIII)

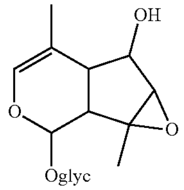

(XIV)

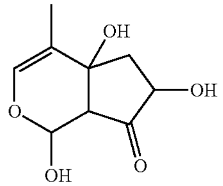

(XV)

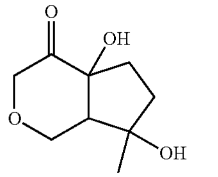

(XVI)

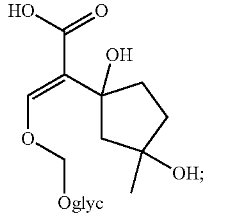

and pharmaceutically acceptable vehicle.

Pharmaceutically Acceptable Vehicle.

To carry out their activity, the compounds of general formula (I), (II) and/or (III) should be administered to an animal organism, a mammal, particularly a human, preferably in the form of a pharmaceutical composition, i.e., associated with pharmaceutically acceptable vehicles which are suitable for each route of administration.

The pharmaceutical compositions of the present invention contain as active ingredient one or more compounds proposed herein, associated with one or more pharmaceutically acceptable vehicles. The active ingredient is commonly mixed, diluted or encapsulated with at least one vehicle.

When the vehicle is a diluent, it may be in the solid, semi-solid or liquid form, acting as a carrier, excipient or medium for the active ingredient. Therefore, the composition can be in the form of tablets, pills, powders, sachets, suspensions, emulsions, solutions, aerosols (in solid or liquid medium), creams, hard or soft capsules, suppositories, injectable solutions.

In the present invention, it is preferably considered as pharmaceutically suitable vehicle any substance different from the compound of general formula (I), (II) or (III), which has been intentionally added thereto to produce a pharmaceutical dosage form appropriate to a route of administration. Non-limiting examples of pharmaceutical excipients suitable for the preparation of pharmaceutical compositions are described in *Handbook of Pharmaceutical Manufacturing Formulations*—Vol. 1 to 6—2004—Sarfaraz K. Niazi—CRC Press e Remington's Pharmaceutical Sciences, Mack Publishing.

Non-limiting examples of routes of administration of the composition comprising the compound of general formula (I), (II) or (III) are the topical, oral, parenteral, nasal, rectal, transmucosal, transdermal routes.

The therapeutic dose to be employed of the compounds of the present invention should be planned and calculated according to the route of administration chosen, the age, the weight and condition of the patient and the severity of the treated disorder. In general, the compounds of the present invention are administered in therapeutically effective doses. Effective doses can be extrapolated from dose-response curves, derived from in vitro or animal models. Typically, the clinician will administer the compound until an appropriate dose to achieve the desired effect.

Process of Production of Active Compounds

The present invention describes in detail the process of production of active compounds of general formula (I), (II) and/or (III). Essentially, the process of production of isolated compounds comprises the step of subjecting at least one ipolamiide compound to at least one heating step at high temperatures, in suitable solvent, for a sufficient time to obtain the compounds derived from ipolamiide of the general formula (I), (II) and/or (III).

In an optional embodiment, the composition of the present invention further comprises the ipolamiide compound.

In a preferred embodiment, the solvent of the present invention comprises water.

Additionally, the present invention describes the process of production of the compounds of general formula (I), (II) and/or (III), comprising the step of subjecting at least one ipolamiide compound to a heating step at high temperatures, in suitable solvent, for a sufficient time to obtain the compounds derived from ipolamiide of the general formula (I), (II) and/or (III).

In a preferred embodiment, high concentrations of the compounds of formula (I), (II) and/or (III) of the present invention are obtained from the total conversion (100%) of the content of ipolamiide used in the respective production process.

Even more preferably, the high concentrations of the present invention comprise about 0.5% to about 45% of each compound (IV to VIII) in a mixture. In this case, the concentrations comprise about 1 to about 5% of the compound IV, preferably 4%; about 15 to about 25% of the compound V, preferably 19%; about 1% to about 6% of the compound VI, preferably 3%; about 35% to about 45% of the compound VII or its isomers (e.g. compound X or compound XI), preferably 37%; about 0.5% to about 4% of the compound VIII or its isomers (e.g. compound IX), preferably 2%.

In a preferred embodiment, the high temperatures of the present invention comprise temperatures above 35° C., more preferably between 35° C. and 165° C.

In another preferred embodiment, the solvent of the present invention comprises other suitable solvents.

In a preferred embodiment, the process of production of the active compounds derived from ipolamiide comprises the step of hydrolysis or solvolysis of ipolamiide.

Even more preferably, the hydrolysis of ipolamiide may be of the acid type. Among the acids suitable for acid hydrolysis of ipolamiide, hydrochloric acid, hydrochloric, sulfuric, nitric, phosphoric and acetic acid can be mentioned, without any specific restrictions to any of them. In a preferred embodiment, in the present invention hydrochloric acid is used.

In an optional embodiment, the hydrolysis of ipolamiide may be of the basic/alkaline type. Among the bases suitable for basic/alkaline hydrolysis of ipolamiide, the alkali-metal hydroxides can be mentioned, without specific restrictions to any of them. In a preferred embodiment, in the present invention sodium hydroxide is used.

In an even more preferred embodiment, the hydrolysis in acidic medium is followed by a hydrolysis in basic/alkaline medium. As an example, we can mention the production process comprising a step of submitting at least one ipolamiide compound to high temperatures and 0.1 N (eq/L) of hydrochloric acid, followed by incubation for different time intervals that can range from 0 to 120 minutes. The hydrolysis is then interrupted by a process of neutralization using, preferably, sodium hydroxide 0.1 N.

In an optional embodiment, the production process of the compounds of general formula (I), (II) and/or (III) comprises a step of hydrolysis of ipolamiide in basic medium, being carried out with aqueous sodium hydroxide solution 0.1 N, maintained at 40° C. for 2 hours.

Production Process of Active Fractions/Extracts Enriched with Ipolamiide Derivatives It was verified by the inventors that certain isolated active compounds of the present invention can be obtained by techniques of molecular design and synthesis. At the same time, we have also specified the advantages of obtaining herbal medicines for the treatment of diseases, since these compound production systems allow a series of productive interactions between the components of the plant and the active compounds, often even synergistically. Thus, to additionally obtain an herbal medicament comprising such active compounds, we have developed an unique production process which allows to obtain an extract enriched with compounds of interest.

As described below, the extract production process of the present invention comprises unique steps that lead to extracts enriched with the ipolamiide derivatives with immunosuppressive activity. We verified the relevance of preselecting input vegetal biomasses containing between 2.5% and 3.5% of ipolamiide, resulting in an extract enriched with ipolamiide and compounds derived from ipolamiide from about 8.5% to about 11.5%. As previously presented, the vegetal biomass containing ipolamiide will be used as starting material for the production process of the extract. Only with the production process of the present invention it is possible to obtain an extract enriched with specific compounds derived from ipolamiide. This enriched extract, further, presents immunosuppressive activity.

Thus, the present invention provides a process to produce standardized extract enriched with ipolamiide derivatives from plants of the genus *Stachytarpheta.*

It is, therefore, an additional object of the present invention a process for production of extract enriched with compounds derived from ipolamiide, comprising essentially the steps of:

a) selecting input vegetal biomass with a content of ipolamiide between 2.5% and 3.5% obtained from plants of the genus *Stachytarpheta;*
b) submitting the selected biomass from a) to oven drying at temperature between 40 to 80° C., until obtaining the humidity stabilization between 10 to 12%;
c) milling the vegetal biomass;
d) performing the extraction of the vegetal biomass through the steps of:
i. heating of the vegetal biomass at a temperature between 70 to 100° C., with constant stirring;
ii. maceration of the vegetal biomass at room temperature;
iii. heating of the vegetal biomass with temperature between 70 to 100° C.

In a preferred embodiment, the process for production of the present invention further comprises the steps of:

iv. filtering and concentration of the extract;
v. drying in Spray Dryer, during 1 to 60 seconds, with inlet temperature between 155 and 165° C. and outlet temperature between 85 to 95° C., coupled to a dehumidifier.

In a preferred embodiment, the process for extraction of the present invention is an aqueous or hydroalcoholic process, even more preferably an aqueous process.

Therefore, the process for production of the present invention allows to obtain a standardized extract enriched with compounds derived from ipolamiide, preferably with a yield of about 8% to about 10%.

It is, therefore, an additional object of the present invention the extract enriched with compounds derived from ipolamiide obtained by the above-mentioned procedure. The standardized extract enriched with compounds derived from ipolamiide of the present invention comprises, preferably, the compounds of formula (I), (II) and/or (III).

The vegetal biomass of the present invention comprises all parts of plants of the genus *Stachytarpheta*. Preferably, the vegetal biomass comprises the aerial parts of the plants, more preferably, the leaves.

In a preferred embodiment, the input vegetal biomass comprises at least one vegetal biomass with uniform content of ipolamiide between 2.5% and 3.5%. In an optional embodiment, the input vegetal biomass comprises more than one vegetal biomass, wherein the different vegetal biomasses have different contents of ipolamiide independently, but together achieve an uniform content of ipolamiide (between 2.5% and 3.5%).

In another preferred embodiment, the actual content of ipolamiide in the input vegetal biomass can be used as a parameter for predicting the theoretical content of ipolamiide and derivatives in the extract obtained. This prediction can be accomplished by a method comprising the step of applying Equation I to some parameters obtained experimentally to find the ideal proportions of ipolamiide in the input vegetal biomass, which preferably projects the content of ipolamiide and derivatives in the extract from 8.5% to 11.5% of. The Equation I is defined below:

% Theoretical content of ipolamiide and derivatives in the extract=% Actual content of ipolamiide in the vegetal biomass×DER/(<actual content of ipolamiide and derivatives in the extract/actual content of ipolamiide in the input vegetal biomass>)±standard deviation (Equation I).

In this way, it is possible to predict the theoretical content of ipolamiide and derivatives in the extract from the actual content of ipolamiide in the input vegetal biomass. Preferably, the ratio between the actual content of ipolamiide and derivatives in the extract/content of ipolamiide in the input vegetal biomass is between about 3.0 and about 3.5.

The present invention further claims standardized extracts enriched with compounds derived from ipolamiide from plants of the genus *Stachytarpheta* obtained from the production process described above.

In an embodiment even more preferred, the plants of the present invention comprise *Stachytarpheta cayennensis.*

The standardized extracts from plants of the genus *Stachytarpheta* are preferably obtained by the production process described above resulting in an extract enriched with ipolamiide and compounds derived from ipolamiide from about 1% to about 20%, preferably from about 8.5% to about 11.5% of content of ipolamiide and derivatives.

It is, therefore, an additional object of the present invention the use of standardized extracts of plants of the genus *Stachytarpheta* containing compounds derived from ipolamiide for the manufacture of a medicament with immunosuppressive activity. More specifically, standardized extracts of plants of the genus *Stachytarpheta* containing compounds derived from ipolamiide of general formula (I), (II) and/or (III) for the manufacture of a medicament with immunosuppressive activity.

It is, therefore, an additional object of the present invention at least one active fraction of extract enriched with compounds derived from ipolamiide. Preferably, at least one fraction comprises at least one compound derived from ipolamiide of formula (I), (II) and/or (III).

In an optional embodiment, the active fraction of enriched extract further comprises ipolamiide.

It is, therefore, an additional object of the present invention the use of at least one standardized fraction enriched with compounds derived from ipolamiide, obtained from plants of the genus *Stachytarpheta* for the manufacture of medicament with immunosuppressive activity.

EXAMPLES—PREFERRED EMBODIMENT

The examples described in the experimental part have the sole purpose of exemplifying one of several ways of carrying out the invention, however, without limiting the scope thereof.

Process of Production and Identification of Active Compounds

The isolated compounds of the present invention are obtained by subjecting the ipolamide compound to 0.1 N hydrochloric acid, at 40° C. and 100° C., for 1 h, 2 h and 5 h. FIG. 3 illustrates the condition at 40° C. From this experiment, we could observe several products from this hydrolysis and, based on chromatograms, identify several derivatives of ipolamiide, such as, for example, the structures described below, as illustrated on FIG. 3.

(IV)

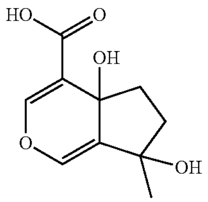

(V)

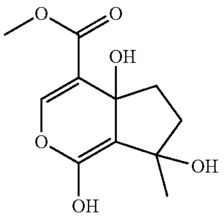

-continued (VI)

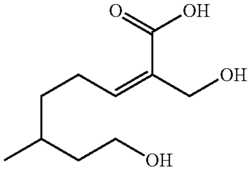

(VII)

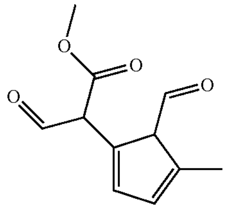

(VIII)

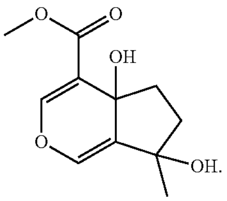

Alternatively, the hydrolysis can be carried out by varying the hydrochloric acid concentration between 0.1 to 1 N and the experimental temperature may vary between 35° C. and 165° C. In addition, the hydrolysis time can vary between 1 minute and 24 hours to facilitate the formation of higher concentrations of certain ipolamiide derivatives.

Process for Obtaining the Extract

According to the present invention, the process for obtaining aqueous extract of *Stachytarpheta cayennensis* rich in ipolamiide derivatives mainly comprised the steps of producing a standardized extract illustrated in the flowchart of FIG. 1 to obtain material for the development of pre-clinical research in immunology.

At first, seeds preferably selected by genotyping of *Stachytarpheta cayennensis* were submitted to a process of seeding for two months in a controlled environment regarding temperature, humidity and light. The seeding was carried out in expanded polystyrene trays, filled with substrate, and kept in this protected environment with controlled irrigation. The seedlings began to appear in 10 to 15 days. The trays remained in these conditions until the seedlings reached size and ideal conditions for permanent transplantation.

The seedlings with an approximate size of 5 to 8 cm in height and with 2 to 3 pairs of definitive leaves were transplanted to the growing site, which preferably had an annual average temperature of 30° C., annual average relative humidity of less than 55%, and in which the soil had preferably, but not limited to, the results of specific chemical and physical soil analyses, for example, acidity, calcium, nitrogen and use of organic fertilization in all areas.

After planting the seedlings, the first harvest was carried out after 6 months, and the other regrowth every 4 months, thus guaranteeing an optimized life cycle for the shrub aiming at maximizing ipolamiide content in the input vegetal biomass.

Following the planting, the vegetal biomass was stabilized through a greenhouse drying process, under defined conditions of temperature and humidity. The plants were dried in dryers with heat exchanger, forced air circulation, and temperature ranging from 50 to 70° C., preferably 60°

C. The drying consisted of the passage of hot air through the plants, removing the humidity, until the vegetal biomass was stabilized with humidity between 10 to 12%. In a preferred embodiment, the drying time occurs from 8 to 20 hours.

As shown in FIG. 1, the vegetal biomass was subjected to the milling process by means of a hammer mill with 1800 RPM and a 19 mm sieve, obtaining a productivity of 50 to 150 kg/hour at room temperature. After milling, the vegetal biomass was submitted to an aqueous extraction at temperature between 80 to 90° C., with constant stirring for 15 min. The amount of extractive solution used should be 10× the amount of vegetal biomass used, guaranteeing exhaustive extraction of the substance of interest in the vegetal biomass.

After the previous step, the material was submitted to the maceration process for 10 h at room temperature. Subsequently, the material was again heated at 80 to 90° C. for 15 min.

The material was filtered on a rotary filter with polyester mesh of 40 um. After the filtration step, the material was concentrated on a "Bernauer" evaporator and/or falling film evaporator to about 30% of total solids.

The product of this step was submitted to drying in Spray Dryer, with inlet temperature between 155 to 165° C. and outlet temperature between 85 to 95° C. coupled to a dehumidifier, preferably of the Bry-Air type, during 20 to 40 seconds, aiming at obtaining the lowest residual humidity content possible (Table 1). This process substantially improves the quality of the enriched extract, since the residual humidity in the material initially compromises the stability of the components of interest, during the shelf life of the vegetal extract/derivative. This extractive process resulted in a ratio of 10 to 12:1 and yield varying between 8 to 10%.

TABLE 1

Humidity content in the extract after drying only and after drying with humidifier

| Humidity content in the extract after drying with SD | Humidity content in the extract after drying with SD + dehumidifier |
|---|---|
| 4.61% | 1.77% |

The extractive process described above guaranteed the exhaustive extraction of ipolamiide to assure the immunosuppressive activity of the extract due to the presence of ipolamiide derivatives generated in the process. Therefore, it was necessary to establish process controls for the input vegetal biomass, so that the actual content of ipolamiide and derivatives in the extract was between 8.5 and 11.5%, as follows in Table 2. The control of ipolamiide in the vegetal biomass ensures the presence of ipolamiide derivatives with immunosuppressive activity in the extract, generated by the process described herein.

TABLE 2

Content of ipolamiide in the vegetal biomass and in the extract.

| Actual content of ipolamiide in the input vegetal biomass | Theoretical content of ipolamiide and derivatives in the extract | Actual content of ipolamiide and derivatives in the extract[a] | Selection of input vegetal biomass |
|---|---|---|---|
| 1.57% | 5.23% (4.44-6.02) | 4.47% | Not selected |
| 2.20% | 7.33% (6.23-8.43) | 7.62% | Not selected |
| 3.00% | 10% (8.5-11.5) | 10.80% | Selected |
| 3.30% | 11% (9.35-12.65) | 11.20% | Selected |
| 3.07% | 10.2% (8.67-11.73) | 8.90% | Selected |
| 3.65% | 12.2% (10.37-14.03) | 12.40% | Not selected |

[a]The agreement between the theoretical and actual contents of ipolamiide and its derivatives in the extract demonstrates the applicability of Equation I.

With this, it was possible to determine a method for predicting the theoretical content of ipolamiide and its derivatives in the enriched active extract. For this purpose, it was used an equation to project the content that would be obtained by the extraction process (theoretical) from the actual content of ipolamiide in the vegetal biomass (Equation I).

% Theoretical content of ipolamiide and derivatives in the extract=% Actual content of ipolamiide in the vegetal biomass×DER/(<actual content of ipolamiide and derivatives in the extract/actual content of ipolamiide in the input vegetal biomass>)±standard deviation (Equation I).

In the above-described equation, DER can be understood as the amount of vegetal biomass required to obtain 1 kilo of native extract. The ratio between the actual content of ipolamiide and derivatives on the extract/content of ipolamiide in the input vegetal biomass is, preferably, between about 3.0 and about 3.5.

Thus, in a prospective way, using the above equation, it is possible to select only the vegetal biomass (whose content of ipolamiide is obtained by analytical methods, such as HPLC) that projects an adequate theoretical content of ipolamiide and derivatives in the extract between 8.5 and 11.5% and discard those that will not project this range. In a novel and inventive manner, it has been verified in the present invention that the relationship between the actual content of ipolamiide and derivatives in the extract and the content of ipolamiide in the input vegetal biomass will, preferably, be between 3.0 and 3.5.

The HPLC analysis comprised the steps of preparing sample solutions and standards, and elution thereof, as follows:

1. Solutions Preparation 1.1—Formic Acid Solution 0.1% (Mobile Phase A): In a 1000 mL volumetric flask containing approximately 800 ml of ultra-pure water, it was added 1 ml of formic acid. The flask volume was filled with ultra-pure water and well homogenized.

1.2—Formic Acid Diluent Solution:Methanol (1:1): In a beaker, it was mixed 50 mL of the 0.1% formic acid solution with 50 mL of methanol.

2. Sample Preparation:

Raw-material (Herbal): 1.0 g of the ground herbal was weighed and transferred to an amber 250 ml Erlenmeyer flask or covered with aluminum foil. 50 mL of distilled water was added and extracted under reflux at 80° C. for 2 hours. The solution was paper-filtered into a 50 mL volumetric flask and filled up with distilled water. It was filtered through 0.22 OR 0.45 μm membrane to an HPLC vial.

3. Standards Preparation:

Ipolamiide standard 100 ppm: 1.0 mg of ipolamiide standard was weighed and transferred to an amber 10 mL volumetric flask. 5 ml of the diluent was added, which was left in an ultrasonic bath for 10 minutes or until complete dissolution. It was filled with the diluent and then there was the homogenization. Humidity analysis by Karl Fischer was performed for the ipolamiide standard.

4. Analysis by HPLC:

4.1—Parameters/Equipment

Column: Zorbax SB-C18 (250 mm×4 mm; 5 um)

Mobile phase: (A) 0.1% formic Acid;

(B) Methanol.

TABLE 3

| Ipolamiide Elution Gradient | | |
|---|---|---|
| Time (min) | (%) A | (%) B |
| 0 | 80 | 20 |
| 27 | 58 | 42 |
| 32 | 58 | 42 |
| 32.1 | 0 | 100 |
| 36 | 0 | 100 |
| 36.1 | 80 | 20 |
| 45 | 80 | 20 |

Flow rate: 1.0 mL/min

Detection: 254 nm.

Analysis time: 45 minutes

Injection volume: 30 μl 4.2—Calculation of Ipolamiide Content $$\text{Content of ipolamiide (\%)} = A \text{ sample} \times M \text{ standard} \times P \text{ standard} \times D \text{ sample} \times (100 - U \text{ standard});$$

$$A \text{ standard} \times M \text{ sample} \times D \text{ standard} \times 10000/100;$$

wherein:

A sample: Peak area of ipolamiide in the sample

M standard: Mass of the standard ipolamiide in mg

P standard: Purity of the standard in decimal

D sample: Dilution of the sample in mL

A standard: Peak area of ipolamiide in the standard

M sample: Mass of the sample used in g

D standard: Dilution of the standard in L

U standard: Humidity of the standard quantified by Karl Fischer

10000: Conversion of units

The result of the content in the extract was given in dry base, that is, the humidity was discounted. Therefore the calculation for the mass of the extract was:

$$M \text{ sample} = \text{Mass} \times (100 - U \text{ sample})/100;$$

wherein:

Mass=Mass of dry extract (in grams)

U sample=Humidity of the dry extract in percentage, according to iT2-052.

5. Analysis by HPLC for Ipolamiide Derivatives 5.1—Parameters/Equipments

Column: Eclipse XDB Agilent—C18 (150×4.6 MM) 5 MICRONS

Mobile phase: (A) 0.1% formic Acid buffer;

(B) Acetonitrile

TABLE 4

| Ipolamiide Derivatives Elution Gradient | | |
|---|---|---|
| Time (min) | (%) A | (%) B |
| 0 | 95 | 5 |
| 5.00 | 90 | 10 |
| 8.00 | 80 | 20 |
| 10.00 | 90 | 10 |
| 12.00 | 95 | 5 |

Flow: 1.2 mL/min

Detection: DAD (205-280 nm).

Analysis time: 15 minutes

Injection volume: 20 μL 5.2 Calculation of Content for Ipolamiide Derivatives

For analysis of a given ipolamiide derivative (Y), we submitted it to a solution with defined concentration. This concentration is directly correlated with the area observed in the chromatogram. This area, when compared with the total area of the chromatogram, multiplied by the concentration previously defined, give us the percentage value of the said derivative (Y) in the sample, as can be seen below:

$$\text{Sample concentration} \times \frac{\text{Derivative } Y \text{ area}}{\text{Total area}} \times 100 = \% \text{ of derivative } Y \text{ content}$$

$$\left(\sum \text{content of derivatives} = \% \text{ total content of ipolamiide derivatives in the sample.}\right)$$

Biological/Immunosuppressive Activity

The evaluation of the in vitro biological activity of the aqueous extract of *Stachytarpheta cayennensis* as well as of ipolamiide and its derivatives was conducted as described below.

The extract of *Stachytarpheta cayennensis*, ipolamiide and derivatives were studied in an experimental in vitro immunological model involving CD8+ T cells and IFNγ. The objective of this study was to evaluate whether the extract and other substances, isolated or mixed, act by blocking the activation of CD8+ T cells and the consequent secretion of IFNγ.

Peripheral blood mononuclear cells (PBMCs) from healthy volunteers were isolated from leukocyte layers by Ficoll-Hystopaque centrifugation. Thereafter, human CD8+ T cells were isolated using the CD8+ T cell isolation kit (Miltenyi Biotec, #130-096-495). These cells ($3\times10^5$ cells/well) were incubated in RPMI+10% of FBS medium, activated with αCD3/CD28 (1 μg/mL) and treated with different concentrations of aqueous extract of *Stachytarpheta cayennensis* standardized in 10% of ipolamiide, isolated ipolamiide, and ipolamiide derivatives obtained by acid hydrolysis to study their effect on the prevention of the CD8+ T cell activation and secretion of IFNγ. For evaluation of cell proliferation, bromodeoxyuridine (BrdU), a thymidine analogue commonly used for proliferation assays, was used as a marker for the proliferation. Specifically, it was evaluated the incorporation of BrdU through the Biotrak ELISA System (GE Healthcare, RPN250) per the manufacturer's instructions. The methodology for quantification of interferon gamma comprised the use of the Human IFNγ ELISA Ready-SET-Go kit (eBiosciences 88-7316-88) and followed the manufacturer's instructions. As illustrated in the graph set of FIG. 2, the aqueous extract of *Stachytarpheta cayennensis* enriched with ipolamiide derivatives blocked the activation of CD8+ T cells induced by αCD3/CD28. Isolated ipolamiide had no effect on the proliferation of CD8+ T cells induced by αCD3/CD28, or the secretion of IFNγ. However, the compounds derived from ipolamiide in a mixture obtained for its acid hydrolysis significantly reduced the CD8+ T cell proliferation and the secretion of IFNγ. The ipolamiide derivatives isolated from this mixture also demonstrated a statistically significant reduction of CD8+ T cell proliferation and of secretion of IFNγ. Tacrolimus, a well-known immunosuppressive agent, was used as a reference compound and as a positive control for the experiment. The effect obtained by tacrolimus was similar to that obtained with hydrolyzed ipolamiide in both cell proliferation and IFNγ production.

Thus, the results showed that the immunosuppressive activity derives from the ipolamiide derivatives and not from the intact molecule. It is important to reinforce that the compounds obtained by the experimental condition of acid hydrolysis of isolated ipolamiide are present in the aqueous extract of *Stachytarpheta cayennensis*, as shown in FIG. 4. However, the presence of such compounds is due to the extraction process used in the present invention.

Those skilled in the art will appreciate the knowledge presented herein and may reproduce the invention in the embodiments presented and in other embodiments, falling within the scope of the appended claims.

The invention claimed is:

1. A compound of compound VII as follows:

(VII)

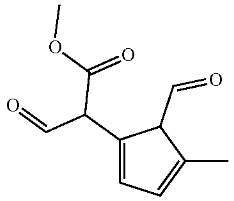

2. A pharmaceutical composition comprising a compound of claim 1, and a pharmaceutically acceptable vehicle.

3. The pharmaceutical composition according to claim 2, further comprising ipolamiide.

4. A process for preparing an extract enriched with a compound of claim 1, comprising:

a) selecting an input vegetal biomass with a content of ipolamiide between 2.5% and 3.5% obtained from plants of the genus *Stachytarpheta;* b) submitting the input vegetal biomass from step a) to oven drying at temperature between 40° C. to 80° C., until obtaining the humidity stabilization between 10 to 12%;

c) milling the oven dried vegetal biomass from step b;

d) performing an extraction of the vegetal biomass through the steps of:

i. heating the vegetal biomass at a temperature between 70° C. to 100° C., with constant stirring;

ii. macerating the vegetal biomass at room temperature; and iii. heating of the vegetal biomass at a temperature between 70° C. to 100° C.

5. The process according to claim 4, further comprising:

iv. filtering and concentrating the extract; and

V. drying in a spray dryer for 1 to 60 seconds, wherein the spray dryer has an inlet temperature between 155° C. and 165° C. and outlet temperature between 85° C. to 95° C., coupled to a dehumidifier.

6. The process according to claim 4, in which the vegetal biomass heating of d) occurs for 5 to 30 minutes.

7. The process according to claim 4, in which the vegetal biomass heating of d) occurs for 5 to 15 hours.

8. The process according to claim 4, in which the input vegetal biomass comprises the aerial parts of the plants of the genus *Stachytarpheta.*

9. The process according to claim 4, in which the plant is *Stachytarpheta cayennensis.*

10. The process according to claim 4, in which the process comprises an aqueous extraction.

11. The process according to claim 4, further comprising predicting the theoretical content of ipolamiide and compound of formula C in the extract from the actual content of ipolamiide in the input vegetal biomass using Equation I:

% Theoretical content of ipolamiide and derivatives in the extract=% Actual content of ipolamiide in the vegetal biomass×DER/(actual content of ipolamiide and derivatives in the extract/actual content of ipolamiide in the input vegetal biomass>)±standard deviation (Equation I), Equation 1;

wherein the compound of formula C has the following formula:

C

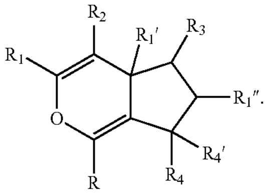

wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$.

12. A composition comprising one or more extracts obtained from the plants of the genus *Stachytarpheta* and the compound according to claim 1.

13. A composition, which is enriched with one or more compounds obtained by the process according to claim 5.

14. The composition of claim 12, which comprises from 1% to 20% of ipolamiide or 1% to 20% of the compound of formula C wherein the compound of formula C has the following formula:

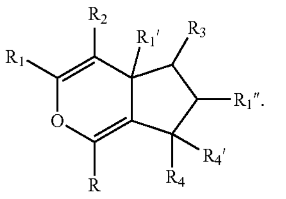

C wherein R corresponds to H, OH, OGlyc (Glycoside); $R_1$, $R_{1'}$, $R_{1''}$ correspond to H, OH; $R_2$ corresponds to H, COOH, $COOCH_3$, $CH_3$, CHO; $R_3$ corresponds to H, OH, $CH_3$; $R_4$, $R_{4'}$ correspond to H, OH, $CH_2OH$, $CH_3$.

15. The compound of claim 1, wherein the compound is prepared by a process comprising:

a) selecting an input vegetal biomass with a content of ipolamiide between 2.5% and 3.5% obtained from one or more plants of the genus *Stachytarpheta;* b) submitting the input vegetal biomass from a) to oven drying at temperature between 40° C. to 80° C., until obtaining humidity stabilization between 10% to 12%;

c) milling the oven dried vegetal biomass from b);

d) preforming an extraction of the vegetal biomass comprising:

i. heating the vegetal biomass at a temperature between 70° C. to 100° C., with constant stirring;

ii. macerating the vegetal biomass at room temperature; and iii. heating the vegetal biomass at a temperature between 70° C. to 100° C.;

thereby obtaining an ipolamiide compound; and e) performing acid hydrolysis on the ipolamiide compound at a temperature between 35-40° C.

* * * * *